United States Patent [19]

Sasaki et al.

[11] Patent Number: 4,939,196
[45] Date of Patent: Jul. 3, 1990

[54] HYDROQUINONE TYPE COMPOUND AND ITS USE AS STABILIZER FOR SYNTHETIC RESIN

[75] Inventors: Manji Sasaki, Ibaraki; Shinichi Yachigo, Toyonaka; Kikumitsu Inoue, Nishinomiya; Shinya Tanaka, Takarazuka; Fumitoshi Kojima, Minoo; Takeshi Takata, Nishinomiya, all of Japan

[73] Assignee: Sumitomo Chemical Company, Limited, Osaka, Japan

[21] Appl. No.: 291,965

[22] Filed: Dec. 30, 1988

[30] Foreign Application Priority Data

Jan. 13, 1988 [JP] Japan .................................... 63-6371

[51] Int. Cl.$^5$ .......................... C07C 65/28; C08K 5/10
[52] U.S. Cl. .................................... 524/291; 524/339; 560/108; 560/140; 568/640
[58] Field of Search ................ 524/291, 339; 568/640; 560/108, 140

[56] References Cited

U.S. PATENT DOCUMENTS

| | | | |
|---|---|---|---|
| 2,133,297 | 10/1938 | Jones | 524/339 |
| 2,591,651 | 4/1952 | Young | 44/78 |
| 3,012,049 | 12/1961 | Bill | 568/640 |
| 3,014,061 | 12/1961 | Irish et al. | 260/462 |
| 3,036,138 | 5/1962 | Mingasson et al. | 524/324 |
| 3,305,522 | 2/1967 | Spacht | 568/790 |
| 3,625,874 | 12/1971 | Cottman et al. | 524/324 |
| 3,637,586 | 1/1972 | Meltsner | 568/640 |
| 3,984,372 | 10/1976 | Cottman | 524/291 |
| 4,168,387 | 9/1979 | Cottman | 560/128 |
| 4,173,541 | 11/1979 | Molt | 524/342 |
| 4,365,032 | 12/1982 | Yosizato et al. | 524/291 |
| 4,525,514 | 6/1985 | Yachigo et al. | 524/291 |
| 4,562,281 | 12/1985 | Takahashi et al. | 560/140 |
| 4,732,923 | 3/1988 | Takata et al. | 524/291 |
| 4,774,274 | 9/1988 | Takata et al. | 524/291 |

*Primary Examiner*—Veronica P. Hoke
*Attorney, Agent, or Firm*—Stevens, Davis, Miller & Mosher

[57] ABSTRACT

A compound represented by the formula of

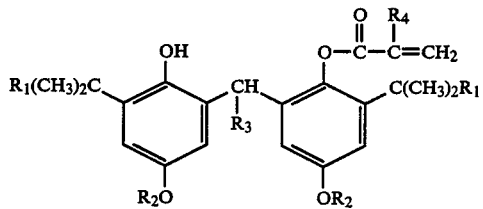

wherein
$R_1$ represents an alkyl having 1 to 5 carbon atoms;
$R_2$ represents an alkyl having 1 to 18 carbon atoms, an alkenyl having 2 to 5 carbon atoms, an aralkyl having 7 to 9 carbon atoms, phenyl, an aliphatic acyl having 2 to 5 carbon atoms, or benzoyl;
$R_3$ represents hydrogen or an alkyl having 1 to 11 carbon atoms; and
$R_4$ represents hydrogen or methyl.

The compound is useful as a stabilizer for synthetic resins such as butadiene polymers. The butadiene polymer containing the compound is stable against thermal deterioration in the absence of oxygen, as well as against thermal oxidative deeterioration and thermal oxidative discoloration.

20 Claims, No Drawings

HYDROQUINONE TYPE COMPOUND AND ITS USE AS STABILIZER FOR SYNTHETIC RESIN

BACKGROUND OF THE INVENTION

The present invention relates to certain novel hydroquinone type compounds and their use as stabilizers for synthetic resins such as butadiene polymers.

In extrusion molding or injection molding of butadiene polymers such as solution-polymerized polybutadiene rubber (BR), solution-polymerized styrene-butadiene copolymer rubber (SBR), and styrene-butadiene block copolymer (SBS) or high-impact polystyrene modified with BR, SBR or SBS, high temperature and high speed processing is required. In such processing, fish eye gel often occurs due to insufficient thermal resistance, resulting in problems such as deterioration of film properties or discoloration. Solution of these problems has been desired.

It has been well known to use various antioxidants of phenol type, phosphorus type and sulfur type during preparation and processing of butadiene polymers. For example, phenolic antioxidants such as 2,6-di-t-butyl-4-methylphenol, 2,2'-methylenebis(6-t-butyl-4-methylphenol), n-octadecyl 3-(3,5-di-t-butyl-4-hydroxyphenyl)propionate, triethylene glycol bis[3-(3-t-butyl-4-hydroxy-5-methylphenyl)propionate], pentaerythrityl 7 tetrakis[3-(3,5-di-t-butyl-4-hydroxyphenyl)propionate] and 1,3,5-trimethyl-2,4,6-tris(3,5-di-t-butyl-4 hydroxybenzyl)benzene are used alone or in combination with phosphorus type antioxidants such as tris(nonylphenyl) phosphite and distearyl pentaerythrityl diphosphite or in combination with sulfur type antioxidants such as dilauryl thiodipropionate, dimyristyl thiodipropionate, distearyl thiodipropionate and pentaerythrityl tetrakis(3-laurylthiopropionate).

However, these methods are not sufficient to prevent thermal deterioration (gelation) which may occur, especially in the absence of oxygen, at high temperature processing of butadiene polymers, although they are effective against thermal oxidative deterioration or discoloration due to thermal oxidation in practical use of the polymers.

Furthermore, U.S. Pat. No. 4,525,514 mentions that 2-t-butyl-6-(3-t-butyl-2-hydroxy-5-methylbenzyl)-4-methylphenyl acrylate is effective as a stabilizer for butadiene polymers. This stabilizer exhibits the effect to prevent thermal deterioration (gelation), especially in the absence of oxygen, at a high temperature process for separation of the polymer from a polymer solution in preparation of butadiene polymers or at high temperature processing of butadiene polymers, but it has become apparent that this stabilizer does not have sufficient effect against thermal oxidative deterioration or discoloration due to the thermal oxidation in practical use of the polymers.

Moreover, as an antioxidant for various synthetic resins for preventing discoloration caused by oxidative deterioration in the presence of oxygen, U.S. Pat. No. 4,365,032 has proposed a monoester compound of 2,2'-alkylidenebis(4,6-di-alkyl substituted phenol). This patent, however, makes no mention of preventing thermal deterioration (gelation) which may occur, especially in the absence of oxygen, at a high temperature process for separating the polymer from a polymer solution in production of butadiene polymers or at high temperature processing of butadiene polymers. Besides, the compounds specifically exemplified in the patent showed no sufficient effect to prevent thermal deterioration, especially in the absence of oxygen, at a high temperature process in the production of butadiene polymers or at high temperature processing of butadiene polymers.

SUMMARY OF THE INVENTION

An object of the present invention is to provide novel compounds which are useful as stabilizers for various synthetic resins such as butadiene polymers.

Another object of the present invention is to stabilize synthetic resins using such compounds.

Further object of the present invention is to stabilize butadiene polymers, especially to prevent thermal deterioration (gelation) in the absence of oxygen, for example, at high temperature processing of the butadiene polymers and besides to prevent thermal oxidative deterioration or discoloration due to thermal oxidation in practical use of the polymers.

As a result of the inventors' research, they have found that a hydroquinone type compound of a specific structure is very effective as a stabilizer for various synthetic resins such as butadiene polymers and especially, butadiene polymers containing such hydroquinone type compound are stable against thermal deterioration in the absence of oxygen and besides are also stable against thermal oxidative deterioration and discoloration caused by thermal oxidation in practical use of the polymers. The present invention has been accomplished based on these findings.

Thus, the present invention provides a compound represented by the formula (I)

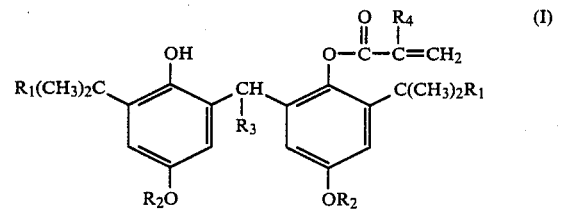

wherein
$R_1$ represents an alkyl having 1 to 5 carbon atoms;
$R_2$ represents an alkyl having 1 to 18 carbon atoms, an alkenyl having 2 to 5 carbon atoms, an aralkyl having 7 to 9 carbon atoms, phenyl, an aliphatic acyl having 2 to 5 carbon atoms, or benzoyl;
$R_3$ represents hydrogen or an alkyl having 1 to 11 carbon atoms; and
$R_4$ represents hydrogen or methyl.

The invention also provides a method for producing a compound of the formula (I) which comprises subjecting to an esterification reaction a compound represented by the formula (II)

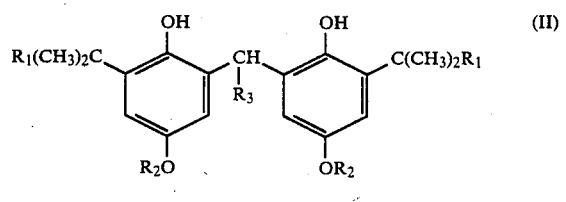

wherein
$R_1$, $R_2$ and $R_3$ have the same meanings as defined above, and an esterifying compound selected from acrylic acid, methacrylic acid, acryloyl chloride, methacryloyl chloride, acryloyl bromide, methacryloyl bromide, acrylic anhydride and methacrylic anhydride.

The invention further provides a method for stabilizing a synthetic resin such as butadiene polymer which comprises incorporating a compound of the formula (I) into the synthetic resin.

The invention still further provides a butadiene polymer composition comprising a butadiene polymer and a compound of the formula (I).

DESCRIPTION OF THE INVENTION

The substituent at 2-position of the hydroquinone type compound represented by the formula (I) is specified to be —$C(CH_3)_2R_1$ containing a quaternary carbon atom in view of preventive effect for gelation of butadiene polymers at high temperatures. $R_1$ in this group is an alkyl of 1–5 carbon atoms such as methyl, ethyl, propyl, t-butyl and 2,2-dimethylpropyl. Among them, methyl and ethyl are preferred and methyl is more preferred.

$R_2$ in the formula (I) is an alkyl of 1–18 carbon atoms, an alkenyl of 2–5 carbon atoms, an aralkyl of 7–9 carbon atoms, phenyl, an aliphatic acyl of 2–5 carbon atoms or benzoyl. The alkyl of 1–18 carbon atoms includes, for example, methyl, ethyl, propyl, butyl, pentyl, octyl, iso-octyl, nonyl, decyl, dodecyl, tetradecyl, hexadecyl, and octadecyl. The alkenyl of 2–5 carbon atoms includes, for example, vinyl, allyl, butenyl and pentenyl. The aralkyl of 7–9 carbon atoms includes, for example, benzyl, α-methylbenzyl and α,α-dimethylbenzyl. The aliphatic acyl of 2–5 carbon atoms includes, for example, acetyl, propionyl, butyroyl and pivaloyl. Among them, methyl, ethyl, butyl, octadecyl, allyl and benzyl are preferred for preventing thermal deterioration of butadiene polymers in the absence of oxygen and thermal oxidative deterioration or discoloration caused by thermal oxidation in practical use of the polymers. More preferred is an alkyl of 1–4 carbon atoms and methyl is especially preferred.

$R_3$ in the formula (I) is hydrogen or an alkyl of 1–11 carbon atoms. Among them, an alkyl of 1–11 carbon atoms is preferred and as examples thereof, mention may be made of methyl, ethyl, propyl, iso-propyl, butyl, pentyl, octyl, iso-octyl, nonyl, decyl and undecyl. Alkyls of less carbon atoms are preferred for preventing gelation of butadiene polymers at high temperatures and specifically, those of 1–4 carbon atoms are preferred. Methyl is especially preferred.

The ester portion containing $R_4$ in the formula (I) affects gelation preventing effect of butadiene polymers at high temperatures and when this ester portion is acrylate group or methacrylate group, the compound exhibits excellent effect to prevent the gelation. Therefore, $R_4$ is hydrogen or methyl and hydrogen is preferred.

Examples of the hydroquinone type compounds represented by the formula (I) of the present invention are shown below. Structural formulas of representative ones among them are shown in Table 1. Number in parentheses shown at the end of the name below corresponds to the compound No. shown in Table 1.

2-t-Butyl-6-[1-(3-t-butyl-2-hydroxy-5-methoxyphenyl)-ethyl]-4-methoxyphenyl acrylate (No. 1), 2-t-Butyl-6-[1-(3-t-butyl-2-hydroxy-5-methoxyphenyl)-ethyl]-4-methoxyphenyl methacrylate (No. 2), 2-t-Butyl-6-(3-t-butyl-2-hydroxy-5-methoxybenzyl)-methoxyphenyl acrylate (No. 3), 2-t-Butyl-6-[1-(3-t-butyl-2-hydroxy-5-methoxyphenyl)-propyl]-4-methoxyphenyl acrylate (No. 4), 2-t-Butyl-6-[1-(3-t-butyl-2-hydroxy-5-methoxyphenyl)-methylpropyl]-4-methoxyphenyl acrylate, 2-t-Butyl-6-[1-(3-t-butyl-2-hydroxy-5-ethoxyphenyl)ethyl]-4-ethoxyphenyl acrylate, 2-t-Butyl-6-[1-(3-t-butyl-2-hydroxy-5-octadecyloxyphenyl)ethyl]-4-octadecyloxyphenyl acrylate (No. 5), 4-Allyloxy-2-[1-(5-allyloxy-3-t-butyl-2-hydroxyphenyl)ethyl]-6-t-butylphenyl acrylate (No. 6), 4-Benzyloxy-2-[1-(5-benzyloxy-3-t-butyl-2-hydroxyphenyl)ethyl]-6-t-butylphenyl acrylate (No. 7), 2-t-Butyl-6-[1-(3-t-butyl-2-hydroxy-5-pivaloyloxyphenyl)ethyl]-4-pivaloyloxyphenyl acrylate (No. 8), 4-Benzoyloxy-2-[1-(5-benzoyloxy-3-t-butyl-2-hydroxyphenyl)ethyl]-6-t-butylphenyl acrylate (No. 9).

TABLE 1

| No. | Structural formula |
|---|---|
| 1 | 2-t-Butyl-6-[1-(3-t-butyl-2-hydroxy-5-methoxyphenyl)ethyl]-4-methoxyphenyl acrylate structure (OH, OCH₃ substituents, CH(CH₃) bridge, O-C(=O)-CH=CH₂ ester) |
| 2 | Corresponding methacrylate structure (O-C(=O)-C(CH₃)=CH₂) |
| 3 | Methylene-bridged (CH₂) bisphenol acrylate with OCH₃ groups |
| 4 | CH(C₂H₅)-bridged analog with OCH₃ groups and acrylate ester |
| 5 | CH(CH₃)-bridged analog with OC₁₈H₃₇ groups and acrylate ester |

TABLE 1-continued

| No. | Structural formula |
|---|---|
| 6 | (structure: bis-phenol with OH, O-C(=O)-CH=CH₂, CH-CH₃ bridge, and two OCH₂CH=CH₂ groups) |
| 7 | (structure: bis-phenol with OH, O-C(=O)-CH=CH₂, CH-CH₃ bridge, and two O-CH₂-phenyl groups) |
| 8 | (structure: bis-phenol with OH, O-C(=O)-CH=CH₂, CH-CH₃ bridge, and two O-C(=O)-t-Bu groups) |
| 9 | (structure: bis-phenol with OH, O-C(=O)-CH=CH₂, CH-CH₃ bridge, and two O-C(=O)-phenyl groups) |

The hydroquinone type compound of the present invention represented by the formula (I) can be produced by subjecting a compound of the above formula (II) and an esterifying compound such as acrylic acid, methacrylic acid, their chlorides, bromides or anhydride, to an esterification reaction.

Similar reactions, although different in starting materials and objective compounds, are disclosed in U.S. Pat. Nos. 4,525,514, 4,562,281 and 4,365,032. That is, in these patents, corresponding monoester compounds are produced using 2,2'-alkylidenebis(4,6-di-alkyl substituted phenol) as starting materials and the objective compounds are different from those of the present invention in substituent at 4-position. However, nearly the same reaction conditions as disclosed in the patents can be applied to produce hydroquinone type compounds of the present invention.

The hydroquinone type compound of the present invention has excellent effect as a stabilizer for various synthetic resins including butadiene polymers which has never been seen in the conventional known compounds. When this hydroquinone type compound is used as a stabilizer, it may be used alone or in admixture with an ordinary carrier which does not affect the properties of the synthetic resins. It may be further mixed with at least one of various additives referred to hereinafter. The following explanation is made referring to an example where the hydroquinone type compound of the present invention is added to butadiene polymers, but it may be added to other synthetic resins in accordance with this explanation. Thus, it is a matter of course that the use of the compound of the present invention should never be limited to the application to butadiene polymers.

Amount of the hydroquinone type compound represented by the formula (I) to be incorporated into a butadiene polymer is preferably 0.05–2 parts by weight, more preferably 0.1–1 part by weight per 100 parts by weight of the butadiene polymer. When it is less than 0.05 part by weight, the desired effect is insufficient and even if it exceeds 2 parts by weight, the corresponding effect cannot be exhibited and this is not economical.

The hydroquinone type compound can be added to the butadiene polymer by dry blending method at the time of processing such as extrusion molding or injection molding.

The present invention can provide a butadiene polymer composition which is stable against thermal deterioration in the absence of oxygen and is also stable against thermal oxidative degradation or discoloration due to thermal oxidation in practical use. Such the composition can be obtained by incorporating the above mentioned hydroquinone type compound into a butadiene polymer as a stabilizer. If necessary, there may be further added other additives such as ultraviolet absorbers, light stabilizers, antioxidants, metal deactivators, metallic soaps, nucleating agents, lubricants, antistatic agents, fire retardants, pigments and fillers.

Examples of these additives are as follows:

Ultraviolet absorbers:
2-Hydroxy-4-methoxybenzophenone,
2-Hydroxy-4-n-octoxybenzophenone,
2-(2-Hydroxy-5-methylphenyl)benzotriazole,
2-(3-t-Butyl-2-hydroxy-5-methylphenyl)-5-chlorobenzotriazole,
2-(3,5-Di-t-butyl-2-hydroxyphenyl)-5-chlorobenzotriazole,
2-(3,5-Di-t-amyl-2-hydroxyphenyl)benzotriazole,
2,4-Di-t-butylphenyl 3,5-di-t-butyl-4-hydroxybenzoate,
[2,2'-Thiobis(4-t-octylphenolate)]/n-butylamine Ni salt.

Hindered amine light stabilizers:
2,2,6,6-Tetramethyl-4-piperidyl benzoate,
Bis(2,2,6,6-tetramethyl-4-piperidyl) sebacate,
Bis(1,2,2,6,6-pentamethyl-4-piperidyl) 2-(3,5-di-t-butyl-4-hydroxybenzyl)-2-n-butylmalonate,
4-[3-(3,5-Di-t-butyl-4-hydroxyphenyl)propionyloxy]-1-[2-{3-(3,5-di-t-butyl-4-hydroxyphenyl)propionyloxy}-ethyl]-2,2,6,6-tetramethylpiperidine,
Polycondensate of dimethyl succinate and 4-hydroxy-1-(2-hydroxyethyl)-2,2,6,6-tetramethylpiperidine,
Poly{[6-(1,1,3,3-tetramethylbutyl)amino-1,3,5-triazine-2,4-diyl][(2,2,6,6-tetramethyl-4piperidyl)imino]hexamethylene[(2,2,6,6-tetramethyl-4-piperidyl)imino]},
Poly{[6-morpholino-1,3,5-triazine-2,4-diyl][(2,2,6,6-tetramethyl-4-piperidyl)imino]hexamethylene[(2,2,6,6-tetramethyl-4-piperidyl)imino]},
2-Methyl-2-(2,2,6,6-tetramethyl-4-piperidyl)amino-N-(2,2,6,6-tetramethyl-4-piperidyl)propionamide.

Phenolic antioxidants:
2,6-Di-t-butyl-4-methylphenol, n-Octadecyl 3-(3,5-di-t-butyl-4-hydroxyphenyl)-propionate, Triethylene glycol bis[3-(3-t-butyl-4-hydroxy-5-methylphenyl)propionate], Pentaerythrityl tetrakis[3-(3,5-di-t-butyl-4-hydroxyphenyl)propionate], 1,3,5-Trimethyl-2,4,6-tris(3,5-di-t-butyl-4-hydroxybenzyl)benzene, 3,9-Bis{2-[3-(3-t-butyl-4-hydroxy-5-methylphenyl)-propionyloxy]-1,1-dimethylethyl}-2,4,8,10-tetraoxaspiro[5.5]undecane.

Sulfur-containing antioxidants:
Dilauryl thiodipropionate,
Dimyristyl thiodipropionate,
Distearyl thiodipropionate,
Pentaerythrityl tetrakis(3-laurylthiopropionate),
3,9-bis(2-laurylthioethyl)-2,4,8,10-tetraoxaspiro[5.5]undecane.

Phosphorus-containing antioxidants:
Distearyl pentaerythrityl diphosphite,
Tris(2,4-di-t-butylphenyl) phosphite,
Tris(2-t-butyl-4-methylphenyl) phosphite,
Bis(2,4-di-t-butylphenyl) pentaerythrityl diphosphite,
Tetrakis(2,4-di-t-butylphenyl) 4,4'-biphenylene diphosphonite,
Bis(2,6-di-t-butyl-4-methylphenyl) pentaerythrityl diphosphite.

As butadiene polymers used in the present invention, mention may be made of, for example, solution polymerized polybutadiene rubber (BR), solution-polymerized styrene-butadiene copolymer rubber (SBR), styrenebutadiene block copolymer (SBS) and high-impact polystyrene (HI-PS) modified with BR, SBR or SBS. These butadiene polymers may be used alone or in combination with other polymers.

The hydroquinone type compound of the formula (I) has excellent performance as a stabilizer for various synthetic resins such as butadiene polymers which has never been seen in the conventional known compounds.

For example, a butadiene polymer composition containing this compound is very stable against gelation caused by thermal deterioration, especially in the absence of oxygen. Therefore, the polymer composition is stable against thermal deterioration which may occur during processing such as injection molding or extrusion molding. For example, the composition can prevent occurrence of fish eye gel during film formation and occurrence of microgel which may cause reduction in gloss or transparency during injection molding, and can provide a high quality product free from discoloration.

Furthermore, the butadiene polymer composition containing the compound is also stable against thermal oxidative deterioration and discoloration due to thermal oxidation and thus, products thereof exhibit high performance free from reduction of properties due to thermal oxidative deterioration and discoloration in practical use.

The present invention will be explained in more detail with reference to preparation examples of the hydroquinone type compound of the present invention, examples of using the hydroquinone type compound in butadiene polymers and comparative examples of using known compounds. However, the present invention should never be limited to these examples.

PREPARATION EXAMPLE 1

In a 2 liter four necked flask equipped with a thermometer, a stirrer, a condenser and a dropping funnel were charged 440.6 g (1.0 mol) of 2,2'-ethylidenebis(6-t-butyl-4-methoxyphenol), 72.1 g (1.0 mol) of acrylic acid, 300 g of toluene and 222.6 g (2.2 mol) of triethylamine. Under a nitrogen atmosphere, 107.3 g (0.7 mol) of phosphorus oxychloride was added dropwise with stirring. After completion of the addition, the flask was kept at 80° C. for 1 hour and then 500 g of water was added and stirred with the reaction mixture at 60° C. followed by separation into layers.

The separated oil layer was repeatedly washed with water until the aqueous layer became nearly neutral and then the oil layer was cooled to 5° C. with stirring to precipitate crystals. Stirring was further continued at the same temperature for sufficient precipitation. The crystals were collected by filtration, washed with cold toluene and dried under reduced pressure to obtain 308 g of white crystalline 2-t-butyl-6-[1-(3-t-butyl-2-hydroxy-5-methoxyphenyl)ethyl]-4-methoxyphenyl acrylate (No. 1 in Table 1). m.p. 114°–115° C.

| | Elemental analysis: | |
|---|---|---|
| | Found | (Calcd.) |
| C: | 73.65% | (73.61%) |
| H: | 8.37% | (8.24%) |

Mass analysis (FD-MS): M/Z 440 (M+)

PREPARATION EXAMPLE 2

Preparation Example 1 was repeated except that 86.1 g (1.0 mol) of methacrylic acid was used in place of acrylic acid, thereby to obtain 186 g of white crystalline 2-t-butyl-6-[1-(3-t-butyl-2-hydroxy-5methoxyphenyl)ethyl]-4-methoxyphenyl methacrylate (No. 2 in Table 1). m.p. 151°–152° C.

| | Elemental analysis: | |
|---|---|---|
| | Found | (Calcd.) |
| C: | 73.84% | (73.98%) |
| H: | 8.44% | (8.43%) |

Mass analysis (FD-MS): M/Z 454 (M+)

PREPARATION EXAMPLES 3-9

Preparation Example 1 was repeated except that each 1.0 mol of the following compounds were used in place of 2,2'-ethylidenebis(6-t-butyl-4-methoxyphenol).

Preparation Example 3: 2,2'-methylenebis(6-t-butyl-4-methoxyphenol).

Preparation Example 4: 2,2'-Propylidenebis(6-t-butyl-4-methoxyphenol).

Preparation Example 5: 2,2'-Ethylidenebis(6-t-butyl-4-octadecyloxyPreparation

Preparation Example 6: 2,2'-Ethylidenebis(4-allyloxy-6-t-butylphenol).

Preparation Example 7: 2,2'-Ethylidenebis(4-benzyloxy-6-t-butylphenol).

Preparation Example 8: 2,2'-Ethylidenebis(6-t-butyl-4-pivaloyloxyPreparation

Preparation Example 9: 2,2'-Ethylidenebis(4-benzoyloxy-6-t-butylphenol).

Name, melting point, color, elemental analysis value and mass analysis value of each of the thus obtained compounds are shown below.

PREPARATION EXAMPLE 3:

2-t-Butyl-6-(3-t-butyl-2-hydroxy-5-methoxybenzyl)-4-methoxyphenyl acrylate (No. 3 in Table 1). m.p. 82°–85° C., white crystal.

| | Elemental analysis: | |
|---|---|---|
| | Found | (Calcd.) |
| C: | 73.45% | (73.22%) |
| H: | 8.24% | (8.03%) |

Mass analysis (FD-MS): M/Z 426 (M+)

Preparation Example 4

2-t-Butyl-6-[1-(3-t-butyl-2-hydroxy-5-methoxyphenyl)propyl]-4-methoxyphenyl acrylate (No. 4 in Table 1). m.p. 96°–97.5° C., white crystal.

| | Elemental analysis: | |
|---|---|---|
| | Found | (Calcd.) |
| C: | 73.86% | (73.98%) |
| H: | 8.43% | (8.43%) |

Mass analysis (FD-MS): M/Z 454 (M+)

PREPARATION EXAMPLE 5

2-t-Butyl-6-[1-(3-t-butyl-2-hydroxy-5-octadecyloxyphenyl)ethyl]-4-octadecyloxyphenyl acrylate (No. 5 in Table 1). m.p. 69°–69.5° C., white crystal.

| | Elemental analysis: | |
|---|---|---|
| | Found | (Calcd.) |
| C: | 79.54% | (79.86%) |
| H: | 11.42% | (11.43%) |

Mass analysis (FD-MS): M/Z 916 (M+)

PREPARATION EXAMPLE 6

4-Allyloxy-2-[1-(5-allyloxy-3-t-butyl-2-hydroxyphenyl)ethyl]-6-t-butylphenyl acrylate (No. 6 in Table 1). m.p. 95°–97.5° C., white crystal.

| | Elemental analysis: | |
|---|---|---|
| | Found | (Calcd.) |
| C: | 75.49% | (75.58%) |
| H: | 8.43% | (8.18%) |

Mass analysis (FD-MS): M/Z 492 (M+)

PREPARATION EXAMPLE 7

4-Benzyloxy-2-[1-(5-benzyloxy-3-t-butyl-2-hydroxyphenyl)ethyl]-6-t-butylphenyl acrylate (No. 7 in Table 1). M.p. 146°–146.5° C., white crystal.

| | Elemental analysis: | |
|---|---|---|
| | Found | (Calcd.) |
| C: | 79.54% | (79.02%) |
| H: | 7.63% | (7.48%) |

Mass analysis (FD-MS): M/Z 592 (M+)

PREPARATION EXAMPLE 8

2-t-Butyl-6-[1-(3-t-butyl-2-hydroxy-5pivaloyloxyphenyl)ethyl]-4-pivaloyloxyphenyl acrylate (No. 8 in Table 1). m.p. 208°–210° C., white crystal.

| | Elemental analysis: | |
|---|---|---|
| | Found | (Calcd.) |
| C: | 72.29% | (72.38%) |
| H: | 8.39% | (8.33%) |

Mass analysis (FD-MS): M/Z 580 (M+)

PREPARATION EXAMPLE 9

4-Benzoyloxy-2-[1-(5-benzoyloxy-3-t-butyl-2-ethyl]-6-t-butylphenyl acrylate (No. 9 in Table 1). m.p. 126.5°–128° C., white crystal.

| | Elemental analysis: | |
|---|---|---|
| | Found | (Calcd.) |
| C: | 77.30% | (75.46%) |
| H: | 6.74% | (6.50%) |

Mass analysis (FD-MS): M/Z 620 (M+)

EXAMPLES 1–2

Commercially available polybutadiene rubber composition (Nippol manufactured by Nippon Zeon Co., Ltd.) was chopped and dipped in acetone for 24 hours at a room temperature to extract stabilizers contained in the rubber followed by removing the acetone. This procedure was repeated several times followed by air-drying to obtain a polybutadiene rubber free from stabilizers.

Into this polybutadiene rubber was incorporated 2-t-butyl-6-[1-(3-t-butyl-2-hydroxy-5-methoxyphenyl)-ethyl]-4-methoxyphenyl acrylate (No. 1 in Table 1) by two-roll mill at 50° C. for 5 minutes. Loading amount of the compound is shown in Table 2 with a unit of part by weight per 100 parts by weight of the polybutadiene rubber.

The resulting polybutadiene rubber compositions were subjected to a kneading test under the following conditions in a nitrogen stream using Laboplastmill (model 40-100 manufactured by Toyo Seiki Co.). Gelation preventing effect at the kneading was evaluated with torque behavior contingent to gelation. The results are shown in Table 2. The effect to prevent the gelation is shown by a gelation time required to reach a peak value of the torque and the longer time means the higher preventive effect.

| [Conditions of the test using Laboplastmill] | |
|---|---|
| (1) Mixer | Model R-60 |
| (2) Range of torque measured | 0–500 kg-cm |
| (3) Amount of charged composition | 30 g |
| (4) Flow rate of nitrogen gas | 1 l/min |
| (5) Test temperature | 180° C. |
| (6) Revolution | 10 rpm during preheating for 3 min; thereafter 60 rpm. |

The resulting polybutadiene rubber compositions were also subjected to an oxygen absorption test using an oxygen absorption apparatus (model CBP-10UV manufactured by Shibayama Kagaku Co.) under the following conditions to evaluate the effect to prevent thermal oxidative deterioration caused by oxygen. The evaluation was performed by measuring an induction period for oxygen absorption. The results are shown in Table 2. The effect to prevent thermal oxidative deterioration is shown by the time required for absorbing a given amount of oxygen from initiation of oxygen absorption (induction period for oxygen absorption). The longer time means the higher preventive effect.

| [Conditions of oxygen absorption test] | |
| --- | --- |
| (1) Amount of composition charged | 1 g |
| (2) Test temperature | 150° C. |
| (3) Amount of oxygen absorbed | 0.9 ml |

The resulting polybutadiene rubber compositions were separately subjected to a thermal oxydative deterioration test in a gear oven (model GHPS-222 manufactured by Tabai Co.) at 150° C. to evaluate the effect to prevent thermal oxidative discoloration due to thermal oxidative deterioration. The evaluation was performed by visually observing the degree of discoloration with time progress. The results are shown in Table 2 by the following criteria.
O: No discoloration
Δ: Discoloration in light yellow
X: Discoloration in yellow

EXAMPLES 3–18

Experiments were effected in the same manner as in Examples 1–2 except that compounds No. 2–No. 9 shown in Table 1 were used in place of 2-t-butyl-6-[1-(3-t-butyl-2-hydroxy-5-methoxyphenyl)ethyl]-4-methoxyphenyl acrylate and the effects to prevent the gelation, thermal oxidative deterioration and thermal oxidative discoloration were evaluated. Loading amount of the test compounds and results of the evaluation are shown in Table 2 in the same manner as in Examples 1–2.

pounds and results of the evaluation are shown in Table 4 in the same manner as in Table 2.

TABLE 3

| No. | Structural formula |
| --- | --- |
| AO-1 | 2,6-di-substituted-4-methylphenol with OH |
| AO-2 | HO-phenyl(X,X substituted)-CH$_2$CH$_2$COC$_{18}$H$_{37}$ (ester) |
| AO-3 | [HO-phenyl(X,X)-CH$_2$CH$_2$COCH$_2$-]$_4$-C |
| AO-4 | bis-phenol: (OH, X,X-substituted phenyl)-CH$_2$-(phenyl X,X, OH)-OCH$_3$/OCH$_3$ |
| AO-5 | (OH, X,X phenyl)-CH$_2$-(phenyl X,X, O-C(=O)-CH=CH$_2$)-OCH$_3$/OCH$_3$ |

TABLE 2

(Test on the compounds of the present invention)

| | | Example | | | | | | | | | | | | | | | | | |
| --- | --- | --- | --- | --- | --- | --- | --- | --- | --- | --- | --- | --- | --- | --- | --- | --- | --- | --- |
| | | 1 | 2 | 3 | 4 | 5 | 6 | 7 | 8 | 9 | 10 | 11 | 12 | 13 | 14 | 15 | 16 | 17 | 18 |
| Compounds of the present | No. 1 | 0.2 | 0.4 | | | | | | | | | | | | | | | | |
| invention (Table 1) | No. 2 | | | 0.2 | 0.4 | | | | | | | | | | | | | | |
| | No. 3 | | | | | 0.2 | 0.4 | | | | | | | | | | | | |
| | No. 4 | | | | | | | 0.2 | 0.4 | | | | | | | | | | |
| | No. 5 | | | | | | | | | 0.2 | 0.4 | | | | | | | | |
| | No. 6 | | | | | | | | | | | 0.2 | 0.4 | | | | | | |
| | No. 7 | | | | | | | | | | | | | 0.2 | 0.4 | | | | |
| | No. 8 | | | | | | | | | | | | | | | 0.2 | 0.4 | | |
| | No. 9 | | | | | | | | | | | | | | | | | 0.2 | 0.4 |
| Gelation time (min) | | 93 | 149 | 87 | 61 | 41 | 70 | 87 | 139 | 60 | 86 | 39 | 59 | 23 | 32 | 51 | 77 | 35 | 52 |
| Induction period for oxygen absorption (min) | | 50 | 71 | 48 | 67 | 36 | 49 | 46 | 64 | 32 | 46 | 27 | 37 | 25 | 35 | 10 | 15 | 9 | 13 |
| Degree of discoloration due to thermal oxidation | After 30 minutes | O | | O | | O | | O | | O | | O | | O | | O | | O | |
| | After 60 minutes | O | | O | | O | | O | | O | | Δ | | Δ | | O | | O | |
| | After 120 minutes | O | | O | | O | | O | | O | | X | | X | | O | | O | |
| | After 180 minutes | O | | Δ | | Δ | | O | | Δ | | X | | X | | Δ | | Δ | |

COMPARATIVE EXAMPLES 1–13

Experiments were made in the same manner as in Examples 1–2 except that the test compounds shown in Table 3 were used in place of 2-t-butyl-6-[1-(3-t-butyl-2-hydroxy-5-methoxyphenyl)ethyl]-4-methoxyphenyl acrylate and the effects to prevent the gelation, thermal oxidative deterioration and thermal oxidative discoloration were evaluated Loading amount of the test com-

TABLE 3-continued

| No. | Structural formula |
|---|---|
| AO-6 | (structure: bis-phenol with OH, CH(CH3) bridge, and O-C(=O)-CH=CH2 acrylate ester group, with t-butyl substituents) |

TABLE 4

(Test on Comparative Compounds)

| | | Comparative Example | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Comparative compounds (Table 3) | AO-1 | 0.4 | 0.8 | | | | | | | | | | | None |
| | AO-2 | | | 0.4 | 0.8 | | | | | | | | | |
| | AO-3 | | | | | 0.4 | 0.8 | | | | | | | |
| | AO-4 | | | | | | | 0.4 | 0.8 | | | | | |
| | AO-5 | | | | | | | | | 0.4 | 0.8 | | | |
| | AO-6 | | | | | | | | | | | 0.2 | 0.4 | |
| Gelation time (min) | | 10 | 14 | 7 | 11 | 9 | 13 | 8 | 11 | 31 | 42 | 43 | 69 | 5 |
| Induction period for oxygen absorption (min) | | 38 | 51 | 23 | 32 | 42 | 59 | 110 | 140 | 17 | 22 | 8 | 11 | 0 |
| Degree of discoloration due to thermal oxidation | After 30 minutes | × | × | ○ | ○ | × | | | Δ | ○ | | | | × |
| | After 60 minutes | × | × | ○ | ○ | × | | | Δ | Δ | | | | × |
| | After 120 minutes | × | × | ○ | ○ | × | | | × | × | | | | × |
| | After 180 minutes | × | × | ○ | ○ | × | | | × | × | | | | × |

What is claimed is:

1. A compound represented by the formula of (structure: bisphenol with OH, $R_1(CH_3)_2C$ and $C(CH_3)_2R_1$ ortho substituents, $R_2O$ and $OR_2$ para substituents, CH($R_3$) bridge, and acrylate ester group $O-C(=O)-C(R_4)=CH_2$)

wherein
$R_1$ represents an alkyl having 1 to 5 carbon atoms;
$R_2$ represents an alkyl having 1 to 18 carbon atoms;
$R_3$ represents hydrogen or an alkyl having 1 to 11 carbon atoms; and
$R_4$ represents hydrogen or methyl.

2. The compound according to claim 1, wherein $R_1$ is methyl or ethyl.

3. The compound according to claim 2, wherein $R_1$ is methyl.

4. The compound according to claim 1, wherein $R_2$ is an alkyl having 1 to 4 carbon atoms.

5. The compound according to claim 4, wherein $R_2$ is methyl.

6. The compound according to claim 1, wherein $R_3$ is an alkyl having 1 to 4 carbon atoms.

7. The compound according to claim 6, wherein $R_3$ is methyl.

8. The compound according to claim 1, wherein $R_4$ is hydrogen.

9. 2-t-butyl-6-[1-(3-t-butyl-2-hydroxy-5-methoxyphenyl)ethyl]-4-methoxyphenyl acrylate.

10. 2-t-butyl-6-[1-(3-t-butyl-2-hydroxy-5-methoxyphenyl)ethyl]-4-methoxyphenyl methacrylate.

11. 2-t-butyl-6-(3-t-butyl-2-hydroxy-5-methoxybenzyl)-4-methoxyphenyl acrylate.

12. 2-t-butyl-6-[1-(3-t-butyl-2-hydroxy-5-octadecyloxyphenyl)ethyl]-4-octadecyloxyphenyl acrylate.

13. 2-t-butyl-6-[1-(3-t-butyl-2-hydroxy-5-methoxyphenyl)propyl]-4-methoxyphenyl acrylate.

14. A stabilizer composition for a synthetic resin comprising a stabilizingly effective amount of a compound of claim 1 and at least one member selected from the group consisting of an inert carrier, ultraviolet light absorbers, light stabilizers, antioxidants, metal deactivators, metallic soaps, nucleating agents, lubricants, antistatic agents, fire retardants, pigments and fillers.

15. A method for stabilizing a synthetic resin which comprises incorporating a compound of claim 1 into the synthetic resin.

16. The method according to claim 15, wherein the synthetic resin is a butadiene polymer.

17. A butadiene polymer composition comprising a butadiene polymer and a compound of claim 1.

18. The composition according to claim 17, wherein the compound is present in an amount of from 0.05 to 2 parts by weight per 100 parts by weight of the butadiene polymer.

19. The composition according to claim 18, wherein the compound of claim 1 is in an amount of from 0.1 to 1 part by weight per 100 parts by weight of the butadiene polymer.

20. The composition according to claim 17, wherein the butadiene polymer is solution-polymerized polybutadiene rubber, solution-polymerized styrene-butadiene copolymer rubber or styrene-butadiene block copolymer.

* * * * *